United States Patent
Schubert et al.

(10) Patent No.: US 7,777,061 B2
(45) Date of Patent: Aug. 17, 2010

(54) ACID-FUNCTIONALIZED ORGANOMETALLIC FRAMEWORK MATERIALS

(75) Inventors: Markus Schubert, Ludwigshafen (DE); Ulrich Mueller, Neustadt (DE); Marco Bosch, Mannheim (DE); Michael Triller, Mannheim (DE); Stephan Hatscher, Syke (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 51 days.

(21) Appl. No.: 12/096,619

(22) PCT Filed: Dec. 12, 2006

(86) PCT No.: PCT/EP2006/069568

§ 371 (c)(1),
(2), (4) Date: Jun. 9, 2008

(87) PCT Pub. No.: WO2007/068681

PCT Pub. Date: Jun. 21, 2007

(65) Prior Publication Data

US 2008/0281116 A1    Nov. 13, 2008

(30) Foreign Application Priority Data

Dec. 16, 2005   (DE)   .................. 10 2005 060 364

(51) Int. Cl.
 *C07F 5/06* (2006.01)
 *C07F 15/00* (2006.01)
 *C07F 1/00* (2006.01)
 *C07F 3/00* (2006.01)

(52) U.S. Cl. .................. 556/176; 556/49; 556/115; 556/125; 556/147

(58) Field of Classification Search .................. 556/49, 556/115, 125, 147, 176
See application file for complete search history.

(56) References Cited

U.S. PATENT DOCUMENTS

| | | | |
|---|---|---|---|
| 5,231,115 A | 7/1993 | Harris |
| 5,648,508 A | 7/1997 | Yaghi |
| 6,329,435 B1 | 12/2001 | Klipper et al. |
| 6,488,859 B2 | 12/2002 | Alexandratos et al. |
| 2004/0081611 A1 | 4/2004 | Muller et al. |

FOREIGN PATENT DOCUMENTS

| | | |
|---|---|---|
| DE | 101 11 230 A 1 | 9/2002 |
| EP | 0 102 544 | 3/1984 |
| EP | 0 200 260 | 4/1986 |

(Continued)

OTHER PUBLICATIONS

Gadzikwa et al., Chemical Communications, vol. 43, pp. 5493-5495 (2008).*

(Continued)

*Primary Examiner*—Porfirio Nazario Gonzalez
(74) *Attorney, Agent, or Firm*—Oblon, Spivak, McClelland, Maier & Neustadt, L.L.P.

(57) ABSTRACT

The present invention relates to porous metal organic frameworks comprising at least one at least bidentate organic compound L coordinated to at least one metal ion M, wherein L has at least one functional group G which bonds noncoordinatively to M and is selected from the group consisting of —$SO_3H$ and —$PO_3H_2$ and their analogues. The invention further provides processes for their preparation and also their use.

9 Claims, 1 Drawing Sheet

FOREIGN PATENT DOCUMENTS

Figure 1:
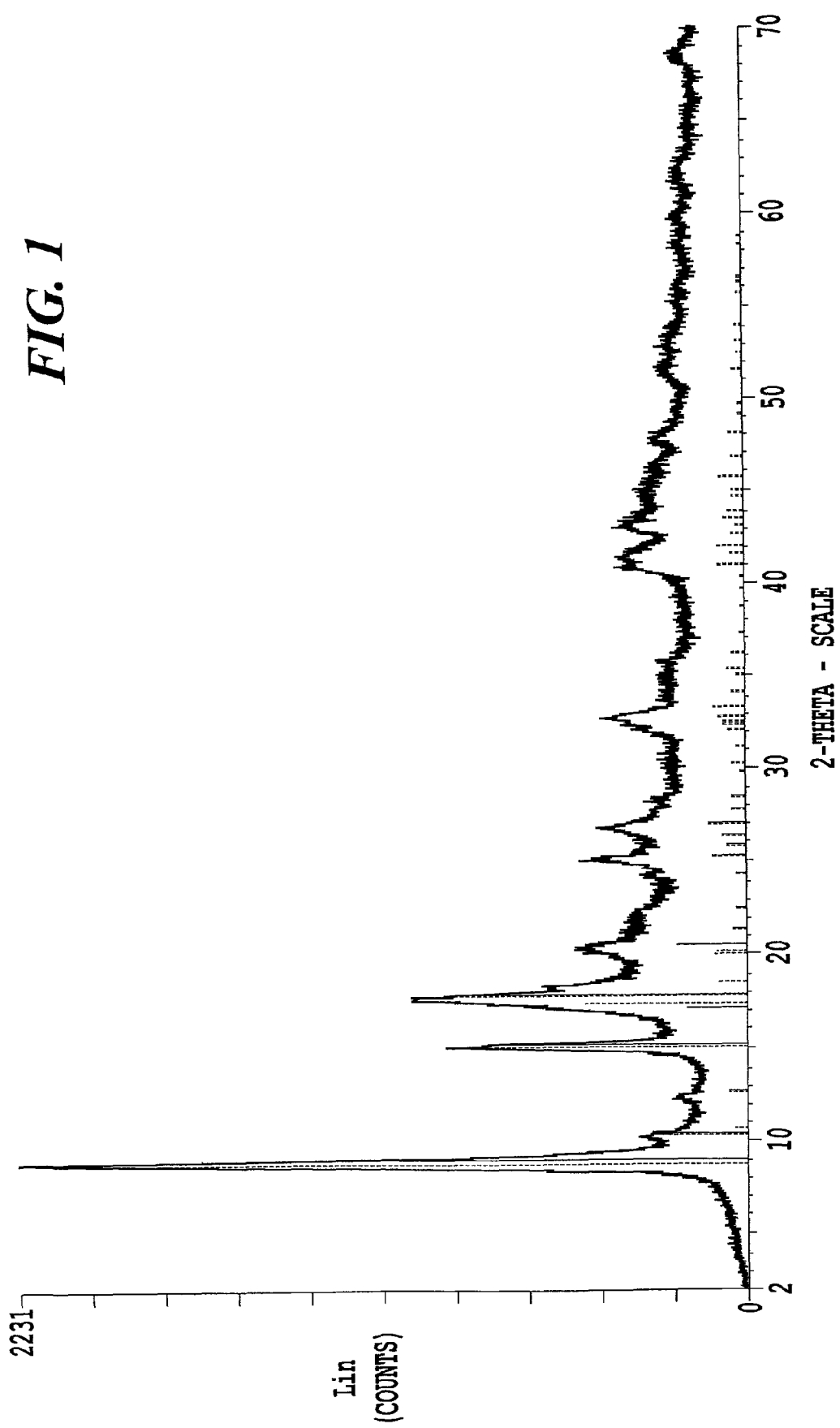

| | | |
|---|---|---|
| EP | 0 389 041 | 3/1990 |
| EP | 0 592 050 A1 | 4/1994 |
| EP | 0 790 253 A2 | 8/1997 |
| ES | 2 200 681 | 1/2004 |
| JP | 03-037156 | 2/1991 |
| WO | WO 94/13584 | 6/1994 |
| WO | WO 94/29408 | 12/1994 |
| WO | WO 95/19222 | 7/1995 |
| WO | WO 2004-084834 A2 | 7/2004 |

OTHER PUBLICATIONS

M. O'Keeffe, "Frameworks for Extended Solids: geometrical Design Principles" Journal of Solid State Chemistry, 152 (2000), 3-20.

Hallian Li, Nature, "Design and synthesis of an exceptionally stable and highly porous metal-organic framework" vol. 402 Nov. 18, (1999), 105-111.

Mohamed Eddaoudi, "Design and systhesis of metlal-carboxylate framewoks with permanent microporosity" Topics in Catalysis 9 (1999) 105-111.

Banglin Chen, et al., "Interwoven Metal-Organic Framework on a Periodic Minimal Surface with Extra-Large Pores" Science 291 (2001), 1021-1023.

Ruibiao Fu, et al. "Nonlinear Optical activity and High Thermal Stability of a New 3D Open-Framework with Interconnected 24-, 16-, and 8-Atom Channels: $(NH_4)Zn[O_3PCH(OH)CO_2]$" Euro. J. Ignorg. Chem. 2005, 3211-3213.

K.S.W. Sing, "Reporting Physisirption Data for Gas/Solid Systems with Special Reference to the Determination of Surface Area and Porosity" Pure & Applied chem. 57 (1985), 603-1023.

Verlag Chemie, "Ullmanns Encyklopadie der technischen Chemie", 4. Auflage, Band 2, S. 313 ff. (1972) (Standard Textbook).

Wan, Shuang-Yi et al.: "Synthesis structure and anion-exchange property of the first example of self-penetrated three-dimensional metal-oraganic framework with flexible three-connecting ligand and nickel (II) perchlorate" Micropourous and Mesopouous Materials (2004), 73 (1-2), 101-108 CODEN: MIMMFJ; ISSN: 1387-1811, 2003.

U.S. Appl. No. 12/668,436, Jan. 11, 2010, Schubert, et al.

U.S. Appl. No. 12/594,604, filed Oct. 5, 2009, Stein, et al.

U.S. Appl. No. 12/597,616, filed Oct. 26, 2009, Schubert, et al.

U.S. Appl. No. 12/601,022, filed Nov. 20, 2009, Schubert, et al.

U.S. Appl. No. 12/600,539, filed Nov. 17, 2009, Schubert, et al.

* cited by examiner

ACID-FUNCTIONALIZED ORGANOMETALLIC FRAMEWORK MATERIALS

The invention relates to metal organic frameworks, processes for preparing them and their use.

Solids having acidic properties are advantageous for numerous applications, one of these applications is ion-exchange chromatography. Here, the solid materials, which are usually referred to as ion exchangers, comprise a component which can reversibly replace ions bound in the exchange-active groups by other ions.

The ion exchangers are divided into cation exchangers and anion exchangers depending on the charge on the exchangeable ion. Cation exchangers known in the prior art are usually made up of a high molecular weight polyvalent anion with movable cations, for example a hydroxy group, a sulfonic acid group, a carboxy group or a phosphonic acid group as exchange-active group. To make exchange particularly efficient, macroporous resins which can sometimes have pore widths of up to 10 nm are of particular interest as solids. To prepare the ion exchangers, the functional groups are typically introduced into polycondensation resins and polymerization resins. Conventional strong acid ion exchangers can, for example, be obtained on the basis of styrene-divinylbenzene copolymers by suspension polymerization and subsequent sulfonation. Commercial ion exchangers are usually spherical particles having a size of from about 0.3 to 1.2 mm. Examples of ion exchangers are obtainable under the trade names Dowex® (Dow), Amberlite®, Amberjet® and Amberlyst® (each from Rohm & Haas) and Lewatit K® (Lanxess).

For catalytic applications in particular, it is important that the sulfonated polymer matrices have a pore structure as described above which allows diffusion of the reactants to and from the exchange-active groups. Macroporous ion exchangers are described, for example, in U.S. Pat. No. 5,231,115 and U.S. Pat. No. 6,329,435. Here, swelling of the actual styrene-divinylbenzene polymer matrix is achieved during the polymerization by addition of additives such as saturated hydrocarbons, saturated alcohols and/or water-soluble polymers so as to make it possible to obtain a pore-like structure. To ensure satisfactory mechanical stability of the macroporous polymer matrix, the proportion of crosslinking monomer (for example divinyl benzene) has to be increased.

The subsequent sulfonation makes possible the derivatization of the copolymer skeleton by sulfonic acid groups. Here, the phenyl groups present are provided with sulfonic acid groups by electrophilic substitution on the aromatic. Ion exchangers based on styrene-divinylbenzene matrices which comprise not only sulfonic acid groups but also phosphonic acid groups are described, for example, in U.S. Pat. No. 6,488,859.

Recently, metal organic frameworks which are conspicuous for their porosity like the abovementioned polymers have been described. The porous metal organic frameworks typically comprise at least one at least bidentate organic compound, usually a dicarboxylic, tricarboxylic or tetracarboxylic acid, coordinated to at least one metal ion. Such metal organic frameworks (MOFs) are described, for example, in U.S. Pat. No. 5,648,508, EP-A 0 790 253, M. O. Keeffe, J. Sol. State Chem. 152 (2000), 2-20; H. P. Li et al., Nature 402 (1999), 276; M. Eddaoudi, Topics in catalysis 9 (1999), 105-111; B. Chen et al., Science 91 (2001), 1021-1023 and DE-A 101 11 230.

Although the porous metal organic frameworks comprise carboxylic acids, they typically have no acid properties. This is because the carboxylic acids participate in the form of their carboxylates in formation of the framework, with the carboxylates accordingly being coordinated to the respective metal and thus not being available as exchange-active acidic group.

Porous metal organic frameworks which comprise the functional groups which are of particular interest for cation exchangers, namely sulfonate and phosphonate, have also been published. Thus, ES-A 2 200 681 discloses rare earth disulfonates and R. Fu et al. describe, in Euro. J. Inorg. Chem. 2005, 3211-3213, frameworks comprising phosphonate groups.

However, in both publications, the acidic functional group is, as indicated above, used for forming the framework. Free exchange-active groups are therefore not available, so that these porous metal organic frameworks, too, are not suitable as, for example, ion exchangers.

There is therefore a need to provide acid-functionalized metal organic frameworks which, for example, can be used as ion exchangers and thus have the advantageous properties of metal organic frameworks in applications which require porous acidic polymers or in which such polymers appear advantageous.

This object is achieved by a porous metal organic framework comprising at least one at least bidentate organic compound L coordinated to at least one metal ion M, wherein L has at least one functional group G which bonds noncoordinatively to M and is selected from the group consisting of —$SO_3H$ and —$PO_3H_2$ and their deprotonated analogues.

It has surprisingly been found that modification of porous metal organic frameworks known per se by the functional group G gives novel porous metal organic frameworks which display acidic properties and can be used, for example, as ion exchangers.

Deprotonated analogues of the group G are —$SO_3^-$, $PO_3H^-$ AND $PO_3^{2-}$. However, it is preferred that at least 50% of the group G is present in protonated form, more preferably at least 75% and the group G is most preferably present in completely protonated form. If G is at least partly present in deprotonated form, alkali metal ions and ammonium ions are suitable counterions.

To form the framework, a metal ion M should be coordinated by at least two molecules of the compound L.

In the porous metal organic framework, the molar ratio of G:M is preferably at least 1:75. The ratio is more preferably at least 1:50, even more preferably at least 1:10.

The molar ratio of G:M is preferably not more than 4:1, more preferably not more than 2:1 and particularly preferably not more than 1:1.

The appropriate ratio of G:M or L:M can be set in the desired way by appropriate reaction conditions in the preparation of the porous metal organic framework of the invention. This can be achieved by methods known to those skilled in the art and depends on the preparative process employed. Thus, for example, the organic compound L can have the functional group G or an analogous group which can be converted into G in the preparation. To set the desired molar ratio of G:M, an organic compound L' which has a similar structure to L but does not have G or a derivative of G can also be used in the reaction of the compound L with M. On the basis of the mixing ratio of L to L', the abovementioned molar ratio of G:M can be set appropriately in the reaction with M.

A further possible way of setting a particular molar ratio is to introduce the group G subsequently, i.e. after a metal organic framework has already been formed. This can be achieved, for example, by sulfonation of an aromatic. In this case, the molar ratio of G:M can be controlled by means of the temperature, the concentration of the sulfonation reagent and the time for which it is allowed to act on the metal organic framework.

There are numerous methods known to those skilled in the art for determining the molar ratio. The ratio can be determined by customary methods such as nuclear magnetic resonance spectroscopy, infrared spectroscopy, thermal desorption of, for example, amines, elemental analysis and/or titration.

The content of the group G in the porous metal organic framework also determines the acid properties of the framework of the invention. Preference is given to the framework having an acid density of at least 0.1 mmol/g. The acid density is preferably at least 1 mmol/g, more preferably at least 2 mmol/g.

The metal component in the framework of the present invention is preferably selected from among groups Ia, IIa, IIIa, IVa to VIIIa and Ib to VIb. Particular preference is given to Mg, Ca, Sr, Ba, Sc, Y, Ti, Zr, Hf, V, Nb, Ta, Cr, Mo, W, Mn, Re, Fe, Ro, Os, Co, Rh, Ir, Ni, Pd, Pt, Cu, Ag, Au, Zn, Cd, Hg, Al, Ga, In, Ti, Si, Ge, Sn, Pb, As, Sb and Bi. Greater preference is given to Zn, Cu, Ni, Pd, Pt, Ru, Rh and Co. Particular preference is given to Zn, Al, Ni and Cu. With regard to ions of these elements, particular mention may be made of $Mg^{2+}$, $Ca^{2+}$, $Sr^{2+}$, $Ba^{2+}$, $Sc^{3+}$, $Y^{3+}$, $Ti^{4+}$, $Zr^{4+}$, $Hf^{4+}$, $V^{4+}$, $V^{3+}$, $V^{2+}$, $Nb^{3+}$, $Ta^{3+}$, $Cr^{3+}$, $Mo^{3+}$, $W^{3+}$, $Mn^{3+}$, $Mn^{2+}$, $Re^{3+}$, $Re^{2+}$, $Fe^{3+}$, $Fe^{2+}$, $Ru^{3+}$, $Ru^{2+}$, $Os^{3+}$, $Os^{2+}$, $Co^{3+}$, $Co^{2+}$, $Rh^{2+}$, $Rh^{+}$, $Ir^{2+}$, $Ir^{+}$, $Ni^{2+}$, $Ni^{+}$, $Pd^{2+}$, $Pd^{+}$, $Pt^{2+}$, $Pt^{+}$, $Cu^{2+}$, $Cu^{+}$, $Ag^{+}$, $Au^{+}$, $Zn^{2+}$, $Cd^{2+}$, $Hg^{2+}$, $Al^{3+}$, $Ga^{3+}$, $I^{3+}$, $T^{13+}$, $Si^{4+}$, $Si^{2+}$, $Ge^{4+}$, $Ge^{2+}$, $Sn^{4+}$, $Sn^{2+}$, $Pb^{4+}$, $Pb^{2+}$, $As^{5+}$, $As^{3+}$, $As^{+}$, $Sb^{5+}$, $Sb^{3+}$, $Sb^{+}$, $Bi^{5+}$, $Bi^{3+}$ and $Bi^{+}$.

Greater preference is give to the metals Sr, Ba, Mo, W, V, Ni, Co, Se, Y, platinum and rare earth metals and also Mg, Ca, Al, Ga, In, Zn, Cu, Fe and Mn.

M is particularly preferably selected from the group consisting of Mg, Ca, Al, Ga, In, Zn, Cu, Fe and Mn. Very particular preference is given to Mg, Al.

The term "at least bidentate organic compound" refers to an organic compound which comprises at least one functional group which is able to form at least two, preferably two, coordinate bonds to a given metal ion and/or form a coordinate bond to each of two or more, preferably two, metal atoms.

As functional groups via which the abovementioned coordinate bonds can be formed, mention may be made by way of example of, in particular: OH, SH, $NH_2$, $NH(-R-H)$, $N(R-H)_2$, $CH_2OH$, $CH_2SH$, $CH_2NH_2$, $CH_2NH(-R-H)$, $CH_2N(-R-H)_2$, $-CO_2H$, $COSH$, $-CS_2H$, $-NO_2$, $-B(OH)_2$, $-SO_3H$, $-Si(OH)_3$, $-Ge(OH)_3$, $-Sn(OH)_3$, $-Si(SH)_4$, $-Ge(SH)_4$, $-Sn(SH)_3$, $-PO_3H_2$, $-AsO_3H$, $-AsO_4H$, $-P(SH)_3$, $-As(SH)_3$, $-CH(RSH)_2$, $-C(RSH)_3$, $-CH(RNH_2)_2$, $-C(RNH_2)_3$, $-CH(ROH)_2$, $-C(ROH)_3$ $-CH(RCN)_2$, $-C(RCN)_3$, where R is preferably, for example, an alkylene group having 1, 2, 3, 4 or 5 carbon atoms, for example a methylene, ethylene, n-propylene, i-propylene, n-butylene, i-butylene, tert-butylene or n-pentylene group, or an aryl group comprising 1 or 2 aromatic rings, for example 2 $C_6$ rings, which may, if appropriate, be fused and may, independently of one another, be appropriately substituted by in each case at least one substituent and/or may, independently of one another comprise in each case at least one heteroatom, for example N, O and/or S. In likewise preferred embodiments, mention may be made of functional groups in which the abovementioned radical R is not present. In this regard, mention may be made of, inter alia, $-CH(SH)_2$, $-C(SH)_3$, $-CH(NH_2)_2$, $CH(NH(R-H))_2$, $CH(N(R-H)_2)_2$, $C(NH(R-H))_3$, $C(N(R-H)_2)_3$, $-C(NH_2)_3$, $-CH(OH)_2$, $-C(OH)_3$, $-CH(CN)_2$, $-C(CN)_3$.

The coordinate bond is preferably not formed via $-SO_3H$ and/or $PO_3H_2$.

The at least two functional groups can in principle be bound to any suitable organic compound as long as it is ensured that the organic compound comprising these functional groups is capable of forming the coordinate bond and of producing the framework.

The organic compounds which comprise at least two functional groups are preferably derived from a saturated or unsaturated aliphatic compound or an aromatic compound or a both aliphatic and aromatic compound.

The aliphatic compound or the aliphatic part of the both aliphatic and aromatic compound can be linear and/or branched and/or cyclic, with a plurality of rings per compound also being possible. The aliphatic compound or the aliphatic part of the both aliphatic and aromatic compound more preferably comprises from 1 to 16, more preferably from 1 to 14, more preferably from 1 to 13, more preferably from 1 to 12, more preferably from 1 to 11 and particularly preferably from 1 to 10, carbon atoms, for example 1, 2, 3, 4, 5, 6, 7, 8, 9 or 10 carbon atoms. Particular preference is here given to, inter alia, methane, adamantane, acetylene, ethylene or butadiene.

The aromatic compound or the aromatic part of the both aromatic and aliphatic compound can have one or more rings, for example two, three, four or five rings, with the rings being able to be present separately from one another and/or at least two rings can be present in fused form. The aromatic compound or the aromatic part of the both aliphatic and aromatic compound particularly preferably has one, two or three rings, with particular preference being given to one or two rings. Furthermore, the rings of said compound can each comprise, independently of one another, at least one heteroatom such as N, O, S, B, P, Si, Al, preferably N, O and/or S. More preferably, the aromatic compound or the aromatic part of the both aromatic and aliphatic compound comprises one or two $C_6$ rings; in the case of two rings, they can be present either separately from one another or in fused form. Aromatic compounds of which particular mention may be made are benzene, naphthalene and/or biphenyl and/or bipyridyl and/or pyridyl.

L is particularly preferably derived from a dicarboxylic, tricarboxylic, tetracarboxylic acid or a sulfur analogue or a diamine. Sulfur analogues are the functional groups $-C(=O)SH$ and its tautomer and $C(=S)SH$. The carboxylic acid or the diamine can, in addition to the functional groups which together with the metal M form the framework, be further substituents which after transformation give the group G. In addition, further substituents can be present. Such substituents are, for example, $-OH$, $-NH_2$, $-SH$, $-NO_2$, halogens such as fluorine, chlorine, bromine or iodine and pseudohalides such as $-CH$, $-CNO$, $-CNS$ or alkyl or alkoxy groups having from 1 to 4 carbon atoms, e.g. methoxy or ethoxy. The group G can also be bound to L via such substituents. It is therefore not necessary for G to be bound to the skeleton of L. As mentioned above, it is not necessary for each at least bidentate organic compound participating in the structure of the framework to have a group G. However, in such a case it is preferred that the at least bidentate organic compound which is different from L differs from L only in the presence of the group G.

Preferred diamines are 1,4-phenylenediamine, 1,2-phenylenediamine, 1,3-phenylenediamine, 1,2-cyclohexanediamine, 1,3-cyclohexanediamine, 1,4-cyclohexanediamine, 3,6-diazaoctane-1,8-diamine, diethylenediamine, ethylenediamine, propylenediamine, trimethylenediamine, 1,1'-biphenyl-4,4'-diamine, 1,7-heptanediamine, isophoronediamine, 2-methylpentamethylenediamine, 4-methyl-1,2-phenyldiamine, 4-methyl-1,3-phenylenediamine, naphthalene-1,5-diamine, naphthalene-1,8-diamine, neopentanediamine, 2-nitro-1,4-phenylenediamine, 4-nitro-1,2-phenylenediamine, 4-nitro-1,3-phenylenediamine, nonamethylenediamine, 1,3-propanediamine, triethylenediamine (DABCO), 3,5-diaminobenzoic acid, 3,4-diaminobenzoic acid, 4,4'-diaminobenzophenone, 1,4-diaminobutane, 2,4-diamino-6-chloropyrimidine, 2,2'-diaminodiethylamine, 1,8-diamino-3,6-dioxaoctane, bis(4-aminophenyl)ether, bis(3-aminophenyl)sulfone, bis(4-aminophenyl)sulfone, 1,6-diaminohexane, 4,5-diamino-6-hydroxy-2-mercaptopyridine, 2,4-diamino-6-hydroxypyrimidine, diaminomaleic dinitrile, 4,6-diamino-2-mercaptopyrimidine, 1,5-diamino-2-methylpentane, 1,9-diaminononane, 1,8-diaminooctane, 2,4-diaminophenol, 2,6-diamino-4-phenyl-1,3,5-triazine, 2,3-diaminopyridine, 2,6-diaminopyridine, 2,3-diaminopropionic acid, 3,4-diaminopyridine, 4,6-diamino-2-pyrimidinethiol, 3,5-diamino-1,2,4-triazole, 1,13-diamino-4,7,10-trioxamidecane and 2,5-diaminovaleric acid.

For the purposes of the present invention, mention may be made by way of example of dicarboxylic acids such as oxalic acid, succinic acid, tartaric acid, 1,4-butanedicarboxylic acid, 1,4-butenedicarboxylic acid, 4-oxopyran-2,6-dicarboxylic acid, 1,6-hexanedicarboxylic acid, decanedicarboxylic acid, 1,8-heptadecanedicarboxylic acid, 1,9-heptadecanedicarboxlic acid, heptadecanedicarboxylic acid, acetylenedicarboxylic acid, 1,2-benzenedicarboxylic acid, 1,3-benzenedicarboxylic acid, 2,3-pyridinedicarboxylic acid, pyridine-2,3-dicarboxylic acid, 1,3-butadiene-1,4-dicarboxylic acid, 1,4-benzenedicarboxylic acid, p-benzenedicarboxylic acid, imidazole-2,4-dicarboxyolic acid, 2-methylquinoline-3,4-dicarboxylic acid, quinoline-2,4-dicarboxylic acid, quinoxaline-2,3-dicarboxylic acid, 6-chloroquinoxaline-2,3-dicarboxylic acid, 4,4'-diaminophenylmethane-3,3'-dicarboxylic acid, quinoline-3,4-dicarboxylic acid, 7-chloro-4-hydroxyquinoline-2,8-dicarboxylic acid, diimidedicarboxylic acid, pyridine-2,6-dicarboxylic acid, 2-methylimidazole-4,5-dicarboxylic acid, thiophene-3,4-dicarboxylic acid, 2-isopropyolimidazole-4,5-dicarboxylic acid, tetrahydropyran-4,4-dicarboxylic acid, perylene-3,9-dicarboxylic acid, perylenedicarboxylic acid, Pluriol E 200-dicarboxylic acid, 3,6-dioxaoctanedicarboxylic acid, 3,5-cyclohexadiene-1,2-dicarboxylic acid, octadicarboxylic acid, pentane-3,3-dicarboxylic acid, 4,4'-diamino-1,1'-biphenyl-3,3'-dicarboxylic acid, 4,4'-diaminobiphenyl-3,3'-dicarboxylic acid, benzidine-3,3'-dicarboxylic acid, 1,4-bis(phenylamino)benzene-2,5-dicarboxuylic acid, 1,1'-binaphthyldicarboxylic acid, 7-chloro-8-methylquinoline-2,3-dicarboxylic acid, 1-anilinoanthraquinone-2,4'-dicarboxylic acid, polytetrahydrofuran-250-dicarboxylic acid, 1,4-bis(carboxymethyl)piperazine-2,3-dicarboxylic acid, 7-chloroquinoline-3,8-dicarboxylic acid, 1-(4-carboxy)phenyl-3-(4-chloro)phenylpyrazoline-4,5-dicarboxylic acid, 1,4,5,6,7,7-hexachloro-5-norbornene-2,3-dicarboxylic acid, phenylindanedicarboxylic acid, 1,3-dibenzyl-2-oxoimidazolidine-4,5-dicarboxylic acid, 1,4-cyclohexanedicarboxylic acid, naphthalene-1,8-dicarboxylic acid, 2-benzoylbenzene-1,3-dicarboxylic acid, 1,3-dibenzyl-2-oxoimidazolidine-4,5-cis-dicarboxylic acid, 2,2'-biquinoline-4,4'-dicarboxylic acid, pyridine-3,4-dicarboxylic acid, 3,6,9-trioxaundecanedicarboxylic acid, hydroxybenzophenonedicarboxylic acid, Pluriol E 300-dicarboxylic acid, Pluriol E 400-dicarboxylic acid, Pluriol E 600-dicarboxylic acid, pyraxole-3,4-dicarboxylic acid, 2,3-pyrazinedicarboxylic acid, 5,6-dimethyl-2,3-pyrazinedicarboxylic acid, (bis(4-aminophenyl)ether)diimidedicarboxylic acid, 4,4'-diaminodiphenylmethanediimidedicarboxylic acid, (bis(4-aminophenyl)sulfone)diimidedicarboxylic acid, 1,4-naphthalenedicarboxylic acid, 2,6-naphthalenedicarboxylic acid, 1,3-adamantanedicarboxylic acid, 1,8-naphthalenedicarboxylic acid, 2,3-naphthalenedicarboxylic acid, 8-methoxy-2,3-naphthalenedicarboxylic acid, 8-nitro-2,3-naphthalenedicarboxylic acid, 8-sulfo-2,3-naphthalenedicarboxylic acid, anthracene-2,3-dicarboxylic acid, 2',3'-diphenyl-p-terphenyl-4,4''-dicarboxylic acid, (diphenyl ether)-4,4'-dicarboxylic acid, imidazole-4,5-dicarboxylic acid, 4(1H)-oxothiochromene-2,8-dicarboxylic acid, 5-tert-butyl-1,3-benzenedicarboxylic acid, 7,8-quinolinedicarboxylic acid, 4,5-imidazoledicarboxylic acid, 4-cyclohexane-1,2-dicarboxylic acid, hexatriacontanedicarboxylic acid, tetradecanedicarboxylic acid, 1,7-heptadicarboxylic acid, 5-hydroxy-1,3-benzenedicarboxylic acid, 2,5-dihydroxy-1,4-benzenedicarboxylic acid, pyrazine-2,3-dicarboxylic acid, furan-2,5-dicarboxylic acid, 1-nonene-6,9-dicarboxylic acid, eicosenedicarboxylic acid, 4,4'-dihydroxydiphenylmethane-3,3'-dicarboxylic acid, 1-amino-4-methyl-9,10-dioxo-9,10-dihydroanthracene-2,3-dicarboxylic acid, 2,5-pyridinedicarboxylic acid, cyclohexene-2,3-dicarboxylic acid, 2,9-dichlorofluorubin-4,11-dicarboxylic acid, 7-chloro-3-methylquinoline-6,8-dicarboxylic acid, 2,4-dichlorobenzophenone-2',5'-dicarboxylic acid, 1,3-benzenedicarboxylic acid, 2,6-pyridinedicarboxylic acid, 1-methylpyrrole-3,4-dicarboxylic acid, 1-benzyl-1H-pyrrole-3,4-dicarboxylic acid, anthraquinone-1,5-dicarboxylic acid, 3,5-pyrazoledicarboxylic acid, 2-nitrobenzene-1,4-dicarboxylic acid, heptane-1,7-dicarboxylic acid, cyclobutane-1,1-dicarboxylic acid, 1,14-tetradecanedicarboxylic acid, 5,6-dehydronorbornane-2,3-dicarboxylic acid, 5-ethyl-2,3-pyridinedicarboxylic acid or camphordicarboxylic acid, tricarboxylic acids such as 2-hydroxy-1,2,3-propanetricarboxylic acid, 7-chloro-2,3,8-quinolinetricarboxylic acid, 1,2,3-, 1,2,4-benzenetricarboxylic acid, 1,2,4-butanetricarboxylic acid, 2-phosphono-1,2,4-butanetricarboxylic acid, 1,3,5-benzenetricarboxylic acid, 1-hydroxy-1,2,3-propanetricarboxylic acid, 4,5-dihydro-4,5-dioxo-1H-pyrrolo[2,3-F]quinoline-2,7,9-tricarboxylic acid, 5-acetyl-3-amino-6-methylbenzene-1,2,4-tricarboxylic acid, 3-amino-5-benzoyl-6-methylbenzene-1,2,4-tricarboxylic acid, 1,2,3-propanetricarboxylic acid or aurinetricarboxylic acid, or tetracarboxylic acids such as 1,1-dioxideoperylo[1,12-BCD]thiophene-3,4,9,10-tetracarboxylic acid, perylenetetracarboxylic acids such as perylene-3,4,9,10-tetracarboxylic acid or (perylene 1,12-sulfone)-3,4,9,10-tetracarboxylic acid, butanetetracarboxylic acids such as 1,2,3,4-butanetetracarboxylic acid or meso-1,2,3,4-butanetetracarboxylic acid, decane-2,4,6,8-tetracarboxylic acid, 1,4,7,10,13,16-hexaoxacyclooctadecane-2,3,11,12-tetracarboxylic acid, 1,2,4,5-benzenetetracarboxylic acid, 1,2,11,12-dodecanetetracarboxylic acid, 1,2,5,6-hexanetetracarboxylic acid, 1,2,7,8-octanetetracarboxylic acid, 1,4,5,8-naphthalenetetracarboxylic acid, 1,2,9,10-decanetetracarboxylic acid, benzophenonetetracarboxylic acid, 3,3',4,4'-benzophenonetetracarboxylic acid, tetrahydrofurantetracarboxylic acid or cyclopentanetetracarboxylic acids such as cyclopentane-1,2,3,4-tetracarboxylic acid.

Very particular preference is given to using optionally at least monosubstituted aromatic dicarboxylic, tricarboxylic or tetracarboxylic acids which have one, two, three, four or more rings and in which each of the rings can comprise at least one heteroatom, with two or more rings being able to comprise identical or different heteroatoms. For example, preference is given to one-ring dicarboxylic acids, one-ring tricarboxylic acids, one-ring tetracarboxylic acids, two-ring dicarboxylic acids, two-ring tricarboxylic acids, two-ring tetracarboxylic acids, three-ring dicarboxylic acids, three-ring tricarboxylic acids, three-ring tetracarboxylic acids, four-ring dicarboxylic acids, four-ring tricarboxylic acids and/or four-ring tetracarboxylic acids. Suitable heteroatoms are, for example, N, O, S, B, P, Si, and preferred heteroatoms here are N, S and/or O, Suitable substituents which may be mentioned in this respect are, inter alia, —OH, a nitro group, an amino group or an alkyl or alkoxy group.

Particular preference is given to using acetylenedicarboxylic acid (ADC), camphordicarboxylic acid, fumaric acid, succinic acid, benzenedicarboxylic acids, naphthalenedicarboxylic acids, biphenyldicarboxylic acids such as 4,4'-biphenyldicarboxylic acid (BPDC), pyrazinedicarboxylic acids such as 2,5-pyrazinedicarboxylic acid, bipyridinedicarboxylic acids such as 2,2'-bipyridinedicarboxylic acids such as 2,2'-bipyridine-5,5'-dicarboxylic acid, benzenetricarboxylic acids such as 1,2,3-, 1,2,4-benzenetricarboxylic acid or 1,3,5-benzenetricarboxylic acid (BTC), benzenetetracarboxylic acid, adamantanetetracarboxylic acid (ATC), adamantanedibenzoate (ADB), benzenetribenzoate (BTB), methanetetrabenzoate (MTB), adamantanetetrabenzoate or dihydroxyterephthalic acids such as 2,5-dihydroxyterephthalic acid (DHBDC) as at least bidentate organic compounds.

Very particular preference is given to using, inter alia, isophthalic acid, terephthalic acid, 2,5-dihydroxyterephthalic acid, 1,2,3-benzenetricarboxylic acid, 1,3,5-benzenetricarboxylic acid, 2,6-naphthalenedicarboxylic acid, 1,4-naphthalenedicarboxylic acid, 1,2,3,4- and 1,2,4,5-benzenetetracarboxylic acid, camphordicarboxylic acid or 2,2'-bipyridine-5, 5'-dicarboxylic acid.

The present invention further provides a process for preparing a framework according to the invention, which comprises the step contacting of a metal ion M with an optionally deprotonated at least bidentate organic compound L which has at least one functional group G which bonds noncoordinatively to M and is selected from the group consisting of —SO$_3$H and —PO$_3$H$_2$ and also their deprotonated analogues to form the framework of the invention.

In the above-described process, the group G is already present in the organic compound L, so that no further conversion steps are necessary. However, it has to be ensured that a sufficient number of the groups G are present in free form and do not participate in framework formation.

The present invention further provides a process for preparing a framework according to the invention, which comprises the steps contacting of a metal ion M with an optionally deprotonated at least bidentate organic compound L' which has at least one S- and/or P-comprising group G' which preferably bonds noncoordinatively to M and conversion of the group G' into a group G on L.

In this process, use is made of a precursor group G' which is introduced in the formation of the skeleton of the at least bidentate organic compound L'. L' is related to L in such a way that the formation of the group G results in conversion of L' into L. Thus, L' differs from L in at least the group G. However, it is also possible for L' to be subjected to further chemical changes during the conversion of G' into G, so that L' can differ from L in further chemical structural features. The group G' is preferably selected so that it cannot participate in framework formation. After formation of the metal organic framework, the group G' can then be converted into the desired group G. Preferred groups G' are either ester derivatives of the group G, i.e. sulfonic esters or phosphonic esters, or halides, anhydrides or acetals thereof which can be converted by simple hydrolysis into the desired group G. Preference is given to sulfonic or phosphonic esters.

Furthermore, the group G' can be a sulfur or phosphorus compound which is present in a lower oxidation state. Any oxidation state is in principle possible here. Conversion into the group G is effected by oxidation methods known to those skilled in the art. Examples of groups G' are thiols, sulfides, disulfides, sulfites or sulfinates. Suitable oxidants are, for example peroxides, air, oxygen, permanganate or chromates.

To introduce the phosphonic acid group, it is generally possible to use similar processes, for example phosphonation or the introduction of a phosphine group. A person skilled in the art will know of further methods.

The present invention further provides a process for preparing a framework according to the invention, which comprises the steps:

reaction of a porous metal organic framework comprising at least one at least bidentate organic compound L' coordinated to at least one metal ion M with an S- and/or P-comprising compound to form a group G on L or a group G' and if G' is present, conversion of G' into G on L.

In this process, the group G is introduced into a porous metal organic framework, with none of the at least bidentate organic compounds L of the framework having a precursor group. Here, the porous metal organic frameworks can be known frameworks of the prior art. One possible way of carrying out the above-described process is direct sulfonation. This can, for example, take place on an aromatic which is part of the organic compound L'. Otherwise, what has been said above applies to L'. L' differs from L at least in the absence of the group G. The aromatic is preferably a phenyl or naphthyl group. However, sulfonation can also be carried out at, for example, a double bond such as a vinylic double bond. Sulfonation reagents can be SO$_3$f, H$_2$SO$_4$, oleum, chlorosulfonic acids or sulfonyl chloride or sulfuryl chloride. Here too, the group G' can, if appropriate, be converted into the group G by hydrolysis and/or oxidation or in another way.

Examples of metal organic frameworks known in the prior art are given below. In addition to the designation of the MOF, the metal and the at least bidentate ligand, the solvent and the cell parameters (angles α, β and γ and the dimensions A, B and C in Å) are indicated. The latter were determined by X-ray diffraction.

| MOF-n | Constituents molar ratio M + L | Solvents | α | β | γ | a | b | c | Space group |
|---|---|---|---|---|---|---|---|---|---|
| MOF-0 | Zn(NO$_3$)$_2$·6H$_2$O H$_3$(BTC) | ethanol | 90 | 90 | 120 | 16.711 | 16.711 | 14.189 | P6(3)/Mcm |
| MOF-2 | Zn(NO$_3$)$_2$·6H$_2$O (0.246 mmol) H$_2$(BDC) 0.241 mmol | DMF toluene | 90 | 102.8 | 90 | 6.718 | 15.49 | 12.43 | P2(1)/n |
| MOF-3 | Zn(NO$_3$)$_2$·6H$_2$O (1.89 mmol) H$_2$(BDC) (1.93 mmol) | DMF MeOH | 99.72 | 111.11 | 108.4 | 9.726 | 9.911 | 10.45 | P-1 |
| MOF-4 | Zn(NO$_3$)$_2$·6H$_2$O (1.00 mmol) H$_3$(BTC) (0.5 mmol) | ethanol | 90 | 90 | 90 | 14.728 | 14.728 | 14.728 | P2(1)3 |
| MOF-5 | Zn(NO$_3$)$_2$·6H$_2$O (2.22 mmol) H$_2$(BDC) (2.17 mmol) | DMF chloro-benzene | 90 | 90 | 90 | 25.669 | 25.669 | 25.669 | Fm-3m |
| MOF-38 | Zn(NO$_3$)$_2$·6H$_2$O (0.27 mmol) H$_3$(BTC) (0.15 mmol) | DMF chloro-benzene | 90 | 90 | 90 | 20.657 | 20.657 | 17.84 | I4cm |
| MOF-31 Zn(ADC)$_2$ | Zn(NO$_3$)$_2$·6H$_2$O 0.4 mmol H$_2$(ADC) 0.8 mmol | ethanol | 90 | 90 | 90 | 10.821 | 10.821 | 10.821 | Pn(-3)m |
| MOF-12 Zn$_2$(ATC) | Zn(NO$_3$)$_2$·6H$_2$O 0.3 mmol H$_4$(ATC) 0.15 mmol | ethanol | 90 | 90 | 90 | 15.745 | 16.907 | 18.167 | Pbca |
| MOF-20 ZnNDC | Zn(NO$_3$)$_2$·6H$_2$O 0.37 mmol H$_2$NDC 0.36 mmol | DMF chloro-benzene | 90 | 92.13 | 90 | 8.13 | 16.444 | 12.807 | P2(1)/c |
| MOF-37 | Zn(NO$_3$)$_2$·6H$_2$O 0.2 mmol H$_2$NDC 0.2 mmol | DEF chloro-benzene | 72.38 | 83.16 | 84.33 | 9.952 | 11.576 | 15.556 | P-1 |
| MOF-8 Tb$_2$(ADC) | Tb(NO$_3$)$_3$·5H$_2$O 0.10 mmol H$_2$ADC 0.20 mmol | DMSO MeOH | 90 | 115.7 | 90 | 19.83 | 9.822 | 19.183 | C2/c |
| MOF-9 Tb$_2$(ADC) | Tb(NO$_3$)$_3$·5H$_2$O 0.08 mmol H$_2$ADB 0.12 mmol | DMSO | 90 | 102.09 | 90 | 27.056 | 16.795 | 28.139 | C2/c |
| MOF-6 | Tb(NO$_3$)$_3$·5H$_2$O 0.30 mmol H$_2$(BDC) 0.30 mmol | DMF MeOH | 90 | 91.28 | 90 | 17.599 | 19.996 | 10.545 | P21/c |
| MOF-7 | Tb(NO$_3$)$_3$·5H$_2$O 0.15 mmol H$_2$(BDC) 0.15 mmol | H$_2$O | 102.3 | 91.12 | 101.5 | 6.142 | 10.069 | 10.096 | P-1 |
| MOF-69A | Zn(NO$_3$)$_2$·6H$_2$O 0.083 mmol 4,4'BPDC 0.041 mmol | DEF H$_2$O$_2$ MeNH$_2$ | 90 | 111.6 | 90 | 23.12 | 20.92 | 12 | C2/c |
| MOF-69B | Zn(NO$_3$)$_2$·6H$_2$O 0.083 mmol 2,6-NCD 0.041 mmol | DEF H$_2$O$_2$ MeNH$_2$ | 90 | 95.3 | 90 | 20.17 | 18.55 | 12.16 | C2/c |
| MOF-11 Cu$_2$(ATC) | Cu(NO$_3$)$_2$·2.5H$_2$O 0.47 mmol H$_2$ATC 0.22 mmol | H$_2$O | 90 | 93.86 | 90 | 12.987 | 11.22 | 11.336 | C2/c |
| MOF-11 Cu$_2$(ATC) dehydr. | | | 90 | 90 | 90 | 8.4671 | 8.4671 | 14.44 | P42/mmc |
| MOF-14 Cu$_3$(BTB) | Cu(NO$_3$)$_2$·2.5H$_2$O 0.28 mmol H$_3$BTB 0.052 mmol | H$_2$O DMF EtOH | 90 | 90 | 90 | 26.946 | 26.946 | 26.946 | Im-3 |

-continued

| MOF-n | Constituents molar ratio M + L | Solvents | α | β | γ | a | b | c | Space group |
|---|---|---|---|---|---|---|---|---|---|
| MOF-32 Cd(ATC) | Cd(NO$_3$)$_2$•4H$_2$O 0.24 mmol H$_4$ATC 0.10 mmol | H$_2$O NaOH | 90 | 90 | 90 | 13.468 | 13.468 | 13.468 | P(−4)3m |
| MOF-33 Zn$_2$(ATB) | ZnCl$_2$ 0.15 mmol H$_4$ATB 0.02 mmol | H$_2$O DMF EtOH | 90 | 90 | 90 | 19.561 | 15.255 | 23.404 | Imma |
| MOF-34 Ni(ATC) | Ni(NO$_3$)$_2$•6H$_2$O 0.24 mmol H$_4$ATC 0.10 mmol | H$_2$O NaOH | 90 | 90 | 90 | 10.066 | 11.163 | 19.201 | P2$_1$2$_1$2$_1$ |
| MOF-36 Zn$_2$(MTB) | Zn(NO$_3$)$_2$•4H$_2$O 0.20 mmol H$_4$MTB 0.04 mmol | H$_2$O DMF | 90 | 90 | 90 | 15.745 | 16.907 | 18.167 | Pbca |
| MOF-39 Zn$_3$O(HBTB) | Zn(NO$_3$)$_2$ 4H$_2$O 0.27 mmol H$_3$BTB 0.07 mmol | H$_2$O DMF EtOH | 90 | 90 | 90 | 17.158 | 21.591 | 25.308 | Pnma |
| NO305 | FeCl$_2$•4H$_2$O 5.03 mmol formic acid. 86.90 mmol | DMF | 90 | 90 | 120 | 8.2692 | 8.2692 | 63.566 | R-3c |
| NO306A | FeCl$_2$•4H$_2$O 5.03 mmol formic acid. 86.90 mmol | DEF | 90 | 90 | 90 | 9.9364 | 18.374 | 18.374 | Pbcn |
| NO29 MOF-0 similar | Mn(Ac)$_2$•4H$_2$O 0.46 mmol H$_3$BTC 0.69 mmol | DMF | 120 | 90 | 90 | 14.16 | 33.521 | 33.521 | P-1 |
| BPR48 A2 | Zn(NO$_3$)$_2$ 6H$_2$O 0.012 mmol H$_2$BDC 0.012 mmol | DMSO toluene | 90 | 90 | 90 | 14.5 | 17.04 | 18.02 | Pbca |
| BPR69 B1 | Cd(NO$_3$)$_2$ 4H$_2$O 0.0212 mmol H$_2$BDC 0.0428 mmol | DMSO | 90 | 98.76 | 90 | 14.16 | 15.72 | 17.66 | Cc |
| BPR92 A2 | Co(NO$_3$)$_2$•6H$_2$O 0.018 mmol H$_2$BDC 0.018 mmol | NMP | 106.3 | 107.63 | 107.2 | 7.5308 | 10.942 | 11.025 | P1 |
| BPR95 C5 | Cd(NO$_3$)$_2$ 4H$_2$O 0.012 mmol H$_2$BDC 0.36 mmol | NMP | 90 | 112.8 | 90 | 14.460 | 11.085 | 15.829 | P2(1)/n |
| Cu C$_6$H$_4$O$_6$ | Cu(NO$_3$)$_2$•2.5H$_2$O 0.370 mmol H$_2$BDC(OH)$_2$ 0.37 mmol | DMF chloro-benzene | 90 | 105.29 | 90 | 15.259 | 14.816 | 14.13 | P2(1)/c |
| M(BTC) MOF-0 similar | Co(SO$_4$) H$_2$O 0.055 mmol H$_3$BTC 0.037 mmol | DMF | | as for MOF-0 | | | | | |
| Tb(C$_6$H$_4$O$_6$) | Tb(NO$_3$)$_3$•5H$_2$O 0.370 mmol H$_2$(C$_6$H$_4$O$_6$) 0.56 mmol | DMF chloro-benzene | 104.6 | 107.9 | 97.147 | 10.491 | 10.981 | 12.541 | P-1 |
| Zn (C$_2$O$_4$) | ZnCl$_2$ 0.370 mmol oxalic acid 0.37 mmol | DMF chloro-benzene | 90 | 120 | 90 | 9.4168 | 9.4168 | 8.464 | P(−3)1m |
| Co(CHO) | Co(NO$_3$)$_2$•5H$_2$O 0.043 mmol formic acid 1.60 mmol | DMF | 90 | 91.32 | 90 | 11.328 | 10.049 | 14.854 | P2(1)/n |
| Cd(CHO) | Cd(NO$_3$)$_2$•4H$_2$O 0.185 mmol formic acid 0.185 mmol | DMF | 90 | 120 | 90 | 8.5168 | 8.5168 | 22.674 | R-3c |

-continued

| MOF-n | Constituents molar ratio M + L | Solvents | α | β | γ | a | b | c | Space group |
|---|---|---|---|---|---|---|---|---|---|
| Cu(C$_3$H$_2$O$_4$) | Cu(NO$_3$)$_2$·2.5H$_2$O 0.043 mmol malonic acid. 0.192 mmol | DMF | 90 | 90 | 90 | 8.366 | 8.366 | 11.919 | P43 |
| Zn$_6$(NDC)$_5$ MOF-48 | Zn(NO$_3$)$_2$·6H$_2$O 0.097 mmol 14 NDC 0.069 mmol | DMF chloro- benzene H$_2$O$_2$ | 90 | 95.902 | 90 | 19.504 | 16.482 | 14.64 | C2/m |
| MOF-47 | Zn(NO$_3$)$_2$ 6H$_2$O 0.185 mmol H$_2$(BDC[CH$_3$]$_4$) 0.185 mmol | DMF chloro- benzene H$_2$O$_2$ | 90 | 92.55 | 90 | 11.303 | 16.029 | 17.535 | P2(1)/c |
| MO25 | Cu(NO$_3$)$_2$·2.5H$_2$O 0.084 mmol BPhDC 0.085 mmol | DMF | 90 | 112.0 | 90 | 23.880 | 16.834 | 18.389 | P2(1)/c |
| Cu-thio | Cu(NO$_3$)$_2$·2.5H$_2$O 0.084 mmol thiophenedicarboxylic acid 0.085 mmol | DEF | 90 | 113.6 | 90 | 15.4747 | 14.514 | 14.032 | P2(1)/c |
| ClBDC1 | Cu(NO$_3$)$_2$·2.5H$_2$O 0.084 mmol H$_2$(BDCCl$_2$) 0.085 mmol | DMF | 90 | 105.6 | 90 | 14.911 | 15.622 | 18.413 | C2/c |
| MOF-101 | Cu(NO$_3$)$_2$·2.5H$_2$O 0.084 mmol BrBDC 0.085 mmol | DMF | 90 | 90 | 90 | 21.607 | 20.607 | 20.073 | Fm3m |
| Zn$_3$(BTC)$_2$ | ZnCl$_2$ 0.033 mmol H$_3$BTC 0.033 mmol | DMF EtOH base added | 90 | 90 | 90 | 26.572 | 26.572 | 26.572 | Fm-3m |
| MOF-j | Co(CH$_3$CO$_2$)$_2$·4H$_2$O (1.65 mmol) H$_3$(BZC) (0.95 mmol) | H$_2$O | 90 | 112.0 | 90 | 17.482 | 12.963 | 6.559 | C2 |
| MOF-n | Zn(NO$_3$)$_2$·6H$_2$O H$_3$(BTC) | ethanol | 90 | 90 | 120 | 16.711 | 16.711 | 14.189 | P6(3)/mcm |
| PbBDC | Pb(NO$_3$)$_2$ (0.181 mmol) H$_2$(BDC) (0.181 mmol) | DMF ethanol | 90 | 102.7 | 90 | 8.3639 | 17.991 | 9.9617 | P2(1)/n |
| Znhex | Zn(NO$_3$)$_2$·6H$_2$O (0.171 mmol) H$_3$BTB (0.114 mmol) | DMF p-xylene ethanol | 90 | 90 | 120 | 37.1165 | 37.117 | 30.019 | P3(1)c |
| AS16 | FeBr$_2$ 0.927 mmol H$_2$(BDC) 0.927 mmol | DMF anhydr. | 90 | 90.13 | 90 | 7.2595 | 8.7894 | 19.484 | P2(1)c |
| AS27-2 | FeBr$_2$ 0.927 mmol H$_3$(BDC) 0.464 mmol | DMF anhydr. | 90 | 90 | 90 | 26.735 | 26.735 | 26.735 | Fm3m |
| AS32 | FeCl$_3$ 1.23 mmol H$_2$(BDC) 1.23 mmol | DMF anhydr. ethanol | 90 | 90 | 120 | 12.535 | 12.535 | 18.479 | P6(2)c |
| AS54-3 | FeBr$_2$ 0.927 BPDC 0.927 mmol | DMF anhydr. n- propanol | 90 | 109.98 | 90 | 12.019 | 15.286 | 14.399 | C2 |
| AS61-4 | FeBr$_2$ 0.927 mmol m-BDC 0.927 mmol | pyridine anhydr. | 90 | 90 | 120 | 13.017 | 13.017 | 14.896 | P6(2)c |
| AS68-7 | FeBr$_2$ 0.927 mmol m-BDC 1.204 mmol | DMF anhydr. pyridine | 90 | 90 | 90 | 18.3407 | 10.036 | 18.039 | Pca2$_1$ |
| Zn(ADC) | Zn(NO$_3$)$_2$·6H$_2$O 0.37 mmol H$_2$(ADC) 0.36 mmol | DMF chloro- benzene | 90 | 99.85 | 90 | 16.764 | 9.349 | 9.635 | C2/c |

-continued

| MOF-n | Constituents molar ratio M + L | Solvents | α | β | γ | a | b | c | Space group |
|---|---|---|---|---|---|---|---|---|---|
| MOF-12 Zn₂ (ATC) | Zn(NO₃)₂·6H₂O 0.30 mmol H₄(ATC) 0.15 mmol | ethanol | 90 | 90 | 90 | 15.745 | 16.907 | 18.167 | Pbca |
| MOF-20 ZnNDC | Zn(NO₃)₂·6H₂O 0.37 mmol H₂NDC 0.36 mmol | DMF chloro-benzene | 90 | 92.13 | 90 | 8.13 | 16.444 | 12.807 | P2(1)/c |
| MOF-37 | Zn(NO₃)₂·6H₂O 0.20 mmol H₂NDC 0.20 mmol | DEF chloro-benzene | 72.38 | 83.16 | 84.33 | 9.952 | 11.576 | 15.556 | P-1 |
| Zn(NDC) (DMSO) | Zn(NO₃)₂·6H₂O H₂NDC | DMSO | 68.08 | 75.33 | 88.31 | 8.631 | 10.207 | 13.114 | P-1 |
| Zn(NDC) | Zn(NO₃)₂·6H₂O H₂NDC | | 90 | 99.2 | 90 | 19.289 | 17.628 | 15.052 | C2/c |
| Zn(HPDC) | Zn(NO₃)₂·4H₂O 0.23 mmol H₂(HPDC) 0.05 mmol | DMF H₂O | 107.9 | 105.06 | 94.4 | 8.326 | 12.085 | 13.767 | P-1 |
| Co(HPDC) | Co(NO₃)₂·6H₂O 0.21 mmol H₂(HPDC) 0.06 mmol | DMF H₂O/ ethanol | 90 | 97.69 | 90 | 29.677 | 9.63 | 7.981 | C2/c |
| Zn₃(PDC) 2.5 | Zn(NO₃)₂·4H₂O 0.17 mmol H₂(HPDC) 0.05 mmol | DMF/ ClBz H₂0/ TEA | 79.34 | 80.8 | 85.83 | 8.564 | 14.046 | 26.428 | P-1 |
| Cd₂ (TPDC)2 | Cd(NO₃)₂·4H₂O 0.06 mmol H₂(HPDC) 0.06 mmol | methanol/ CHP H₂O | 70.59 | 72.75 | 87.14 | 10.102 | 14.412 | 14.964 | P-1 |
| Tb(PDC)1.5 | Tb(NO₃)₃·5H₂O 0.21 mmol H₂(PDC) 0.034 mmol | DMF H₂O/ ethanol | 109.8 | 103.61 | 100.14 | 9.829 | 12.11 | 14.628 | P-1 |
| ZnDBP | Zn(NO₃)₂·6H₂O 0.05 mmol dibenzyl phosphate 0.10 mmol | MeOH | 90 | 93.67 | 90 | 9.254 | 10.762 | 27.93 | P2/n |
| Zn₃(BPDC) | ZnBr₂ 0.021 mmol 4,4'BPDC 0.005 mmol | DMF | 90 | 102.76 | 90 | 11.49 | 14.79 | 19.18 | P21/n |
| CdBDC | Cd(NO₃)₂·4H₂O 0.100 mmol H₂(BDC) 0.401 mmol | DMF Na₂SiO₃ (aq) | 90 | 95.85 | 90 | 11.2 | 11.11 | 16.71 | P21/n |
| Cd-mBDC | Cd(NO₃)₂·4H₂O 0.009 mmol H₂(mBDC) 0.018 mmol | DMF MeNH₂ | 90 | 101.1 | 90 | 13.69 | 18.25 | 14.91 | C2/c |
| Zn₄OBNDC | Zn(NO₃)₂·6H₂O 0.041 mmol BNDC | DEF MeNH₂ H₂O₂ | 90 | 90 | 90 | 22.35 | 26.05 | 59.56 | Fmmm |
| Eu(TCA) | Eu(NO₃)₃·6H₂O 0.14 mmol TCA 0.026 mmol | DMF chloro-benzene | 90 | 90 | 90 | 23.325 | 23.325 | 23.325 | Pm-3n |
| Tb(TCA) | Tb(NO₃)₃·6H₂O 0.069 mmol TCA 0.026 mmol | DMF chloro-benzene | 90 | 90 | 90 | 23.272 | 23.272 | 23.372 | Pm-3n |
| Formate | Ce(NO₃)₃·6H₂O 0.138 mmol formic acid 0.43 mmol | H₂O ethanol | 90 | 90 | 120 | 10.668 | 10.667 | 4.107 | R-3m |
| | FeCl₂·4H₂O 5.03 mmol formic acid 86.90 mmol | DMF | 90 | 90 | 120 | 8.2692 | 8.2692 | 63.566 | R-3c |
| | FeCl₂·4H₂O 5.03 mmol formic acid | DEF | 90 | 90 | 90 | 9.9364 | 18.374 | 18.374 | Pbcn |

-continued

| MOF-n | Constituents molar ratio M + L | Solvents | α | β | γ | a | b | c | Space group |
|---|---|---|---|---|---|---|---|---|---|
| | 86.90 mmol FeCl$_2$•4H$_2$O 5.03 mmol formic acid | DEF | 90 | 90 | 90 | 8.335 | 8.335 | 13.34 | P-31c |
| NO330 | 86.90 mmol FeCl$_2$•4H$_2$O 0.50 mmol formic acid | formamide | 90 | 90 | 90 | 8.7749 | 11.655 | 8.3297 | Pnna |
| NO332 | 8.69 mmol FeCl$_2$•4H$_2$O 0.50 mmol formic acid | DIP | 90 | 90 | 90 | 10.0313 | 18.808 | 18.355 | Pbcn |
| NO333 | 8.69 mmol FeCl$_2$•4H$_2$O 0.50 mmol formic acid | DBF | 90 | 90 | 90 | 45.2754 | 23.861 | 12.441 | Cmcm |
| NO335 | 8.69 mmol FeCl$_2$•4H$_2$O 0.50 mmol formic acid | CHF | 90 | 91.372 | 90 | 11.5964 | 10.187 | 14.945 | P21/n |
| NO336 | 8.69 mmol FeCl$_2$•4H$_2$O 0.50 mmol formic acid | MFA | 90 | 90 | 90 | 11.7945 | 48.843 | 8.4136 | Pbcm |
| NO13 | 8.69 mmol Mn(Ac)$_2$•4H$_2$O 0.46 mmol benzoic acid 0.92 mmol bipyridine 0.46 mmol | ethanol | 90 | 90 | 90 | 18.66 | 11.762 | 9.418 | Pbcn |
| NO29 MOF-0 similar | Mn(Ac)$_2$•4H$_2$O 0.46 mmol H$_3$BTC 0.69 mmol | DMF | 120 | 90 | 90 | 14.16 | 33.521 | 33.521 | P-1 |
| Mn(hfac)$_2$ (O$_2$CC$_6$H$_5$) | Mn(Ac)$_2$•4H$_2$O 0.46 mmol Hfac 0.92 mmol bipyridine 0.46 mmol | ether | 90 | 95.32 | 90 | 9.572 | 17.162 | 14.041 | C2/c |
| BPR43G2 | Zn(NO$_3$)$_2$•6H$_2$O 0.0288 mmol H$_2$BDC 0.0072 mmol | DMF CH$_3$CN | 90 | 91.37 | 90 | 17.96 | 6.38 | 7.19 | C2/c |
| BPR48A2 | Zn(NO$_3$)$_2$ 6H$_2$O 0.012 mmol H$_2$BDC 0.012 mmol | DMSO toluene | 90 | 90 | 90 | 14.5 | 17.04 | 18.02 | Pbca |
| BPR49B1 | Zn(NO$_3$)$_2$ 6H$_2$O 0.024 mmol H$_2$BDC 0.048 mmol | DMSO methanol | 90 | 91.172 | 90 | 33.181 | 9.824 | 17.884 | C2/c |
| BPR56E1 | Zn(NO$_3$)$_2$ 6H$_2$O 0.012 mmol H$_2$BDC 0.024 mmol | DMSO n-propanol | 90 | 90.096 | 90 | 14.5873 | 14.153 | 17.183 | P2(1)/n |
| BPR68D10 | Zn(NO$_3$)$_2$ 6H$_2$O 0.0016 mmol H$_3$BTC 0.0064 mmol | DMSO benzene | 90 | 95.316 | 90 | 10.0627 | 10.17 | 16.413 | P2(1)/c |
| BPR69B1 | Cd(NO$_3$)$_2$ 4H$_2$O 0.0212 mmol H$_2$BDC 0.0428 mmol | DMSO | 90 | 98.76 | 90 | 14.16 | 15.72 | 17.66 | Cc |
| BPR73E4 | Cd(NO$_3$)$_2$ 4H$_2$O 0.006 mmol H$_2$BDC 0.003 mmol | DMSO toluene | 90 | 92.324 | 90 | 8.7231 | 7.0568 | 18.438 | P2(1)/n |
| BPR76D5 | Zn(NO$_3$)$_2$ 6H$_2$O 0.0009 mmol H$_2$BzPDC 0.0036 mmol | DMSO | 90 | 104.17 | 90 | 14.4191 | 6.2599 | 7.0611 | Pc |
| BPR80B5 | Cd(NO$_3$)$_2$•4H$_2$O 0.018 mmol | DMF | 90 | 115.11 | 90 | 28.049 | 9.184 | 17.837 | C2/c |

-continued

| MOF-n | Constituents molar ratio M + L | Solvents | α | β | γ | a | b | c | Space group |
|---|---|---|---|---|---|---|---|---|---|
| BPR80H5 | H$_2$BDC 0.036 mmol Cd(NO$_3$)$_2$ 4H$_2$O 0.027 mmol | DMF | 90 | 119.06 | 90 | 11.4746 | 6.2151 | 17.268 | P2/c |
| BPR82C6 | H$_2$BDC 0.027 mmol Cd(NO$_3$)$_2$ 4H$_2$O 0.0068 mmol | DMF | 90 | 90 | 90 | 9.7721 | 21.142 | 27.77 | Fdd2 |
| BPR86C3 | H$_2$BDC 0.202 mmol Co(NO$_3$)$_2$ 6H$_2$O 0.0025 mmol | DMF | 90 | 90 | 90 | 18.3449 | 10.031 | 17.983 | Pca2(1) |
| BPR86H6 | H$_2$BDC 0.075 mmol Cd(NO$_3$)$_2$•6H$_2$O 0.010 mmol | DMF | 80.98 | 89.69 | 83.412 | 9.8752 | 10.263 | 15.362 | P-1 |
| BPR95A2 | H$_2$BDC 0.010 mmol Co(NO$_3$)$_2$ 6H$_2$O Zn(NO$_3$)$_2$ 6H$_2$O 0.012 mmol | NMP NMP | 106.3 90 | 107.63 102.9 | 107.2 90 | 7.5308 7.4502 | 10.942 13.767 | 11.025 12.713 | P1 P2(1)/c |
| CuC$_6$F$_4$O$_4$ | H$_2$BDC 0.012 mmol Cu(NO$_3$)$_2$•2.5H$_2$O 0.370 mmol H$_2$BDC(OH)$_2$ 0.37 mmol | DMF chloro-benzene | 90 | 98.834 | 90 | 10.9675 | 24.43 | 22.553 | P2(1)/n |
| Fe formic | FeCl$_2$•4H$_2$O 0.370 mmol formic acid 0.37 mmol | DMF | 90 | 91.543 | 90 | 11.495 | 9.963 | 14.48 | P2(1)/n |
| Mg formic | Mg(NO$_3$)$_2$•6H$_2$O 0.370 mmol formic acid 0.37 mmol | DMF | 90 | 91.359 | 90 | 11.383 | 9.932 | 14.656 | P2(1)/n |
| MgC$_6$H$_4$O$_6$ | Mg(NO$_3$)$_2$•6H$_2$O 0.370 mmol H$_2$BDC(OH)$_2$ 0.37 mmol | DMF | 90 | 96.624 | 90 | 17.245 | 9.943 | 9.273 | C2/c |
| Zn C$_2$H$_4$BDC MOF-38 | ZnCl$_2$ 0.44 mmol CBBDC 0.261 mmol | DMF | 90 | 94.714 | 90 | 7.3386 | 16.834 | 12.52 | P2(1)/n |
| MOF-49 | ZnCl$_2$ 0.44 mmol m-BDC 0.261 mmol | DMF CH$_3$CN | 90 | 93.459 | 90 | 13.509 | 11.984 | 27.039 | P2/c |
| MOF-26 | Cu(NO$_3$)$_2$•5H$_2$O 0.084 mmol DCPE 0.085 mmol | DMF | 90 | 95.607 | 90 | 20.8797 | 16.017 | 26.176 | P2(1)/n |
| MOF-112 | Cu(NO$_3$)$_2$•2.5H$_2$O 0.084 mmol o-Br-m-BDC 0.085 mmol | DMF ethanol | 90 | 107.49 | 90 | 29.3241 | 21.297 | 18.069 | C2/c |
| MOF-109 | Cu(NO$_3$)$_2$•2.5H$_2$O 0.084 mmol KDB 0.085 mmol | DMF | 90 | 111.98 | 90 | 23.8801 | 16.834 | 18.389 | P2(1)/c |
| MOF-111 | Cu(NO$_3$)$_2$•2.5H$_2$O 0.084 mmol o-BrBDC 0.085 mmol | DMF ethanol | 90 | 102.16 | 90 | 10.6767 | 18.781 | 21.052 | C2/c |
| MOF-110 | Cu(NO$_3$)$_2$•2.5H$_2$O 0.084 mmol thiophene-dicarboxylic acid 0.085 mmol | DMF | 90 | 90 | 120 | 20.0652 | 20.065 | 20.747 | R-3/m |
| MOF-107 | Cu(NO$_3$)$_2$•2.5H$_2$O 0.084 mmol thiophene-dicarboxylic acid 0.085 mmol | DEF | 104.8 | 97.075 | 95.206 | 11.032 | 18.067 | 18.452 | P-1 |
| MOF-108 | Cu(NO$_3$)$_2$•2.5H$_2$O 0.084 mmol | DBF/ methanol | 90 | 113.63 | 90 | 15.4747 | 14.514 | 14.032 | C2/c |

| MOF-n | Constituents molar ratio M + L | Solvents | α | β | γ | a | b | c | Space group |
|---|---|---|---|---|---|---|---|---|---|
| MOF-102 | thiophene-dicarboxylic acid 0.085 mmol Cu(NO$_3$)$_2$•2.5H$_2$O 0.084 mmol | DMF | 91.63 | 106.24 | 112.01 | 9.3845 | 10.794 | 10.831 | P-1 |
| Clbdc1 | H$_2$(BDCCl$_2$) 0.085 mmol Cu(NO$_3$)$_2$•2.5H$_2$O 0.084 mmol | DEF | 90 | 105.56 | 90 | 14.911 | 15.622 | 18.413 | P-1 |
| Cu(NMOP) | H$_2$(BDCCl$_2$) 0.085 mmol Cu(NO$_3$)$_2$•2.5H$_2$O 0.084 mmol NBDC 0.085 mmol | DMF | 90 | 102.37 | 90 | 14.9238 | 18.727 | 15.529 | P2(1)/m |
| Tb(BTC) | Tb(NO$_3$)$_3$•5H$_2$O 0.033 mmol H$_3$BTC 0.033 mmol | DMF | 90 | 106.02 | 90 | 18.6986 | 11.368 | 19.721 | |
| Zn$_3$(BTC)$_2$ Honk | ZnCl$_2$ 0.033 mmol H$_3$BTC 0.033 mmol | DMF ethanol | 90 | 90 | 90 | 26.572 | 26.572 | 26.572 | Fm-3m |
| Zn$_4$O(NDC) | Zn(NO$_3$)$_2$•4H$_2$O 0.066 mmol 14NDC 0.066 mmol | DMF ethanol | 90 | 90 | 90 | 41.5594 | 18.818 | 17.574 | aba2 |
| CdTDC | Cd(NO$_3$)$_2$•4H$_2$O 0.014 mmol thiophene 0.040 mmol DABCO 0.020 mmol | DMF H$_2$O | 90 | 90 | 90 | 12.173 | 10.485 | 7.33 | Pmma |
| IRMOF-2 | Zn(NO$_3$)$_2$•4H$_2$O 0.160 mmol o-Br-BDC 0.60 mmol | DEF | 90 | 90 | 90 | 25.772 | 25.772 | 25.772 | Fm-3m |
| IRMOF-3 | Zn(NO$_3$)$_2$•4H$_2$O 0.20 mmol H$_2$N-BDC 0.60 mmol | DEF ethanol | 90 | 90 | 90 | 25.747 | 25.747 | 25.747 | Fm-3m |
| IRMOF-4 | Zn(NO$_3$)$_2$•4H$_2$O 0.11 mmol [C$_3$H$_7$O]$_2$-BDC 0.48 mmol | DEF | 90 | 90 | 90 | 25.849 | 25.849 | 25.849 | Fm-3m |
| IRMOF-5 | Zn(NO$_3$)$_2$•4H$_2$O 0.13 mmol [C$_5$H$_{11}$O]$_2$-BDC 0.50 mmol | DEF | 90 | 90 | 90 | 12.882 | 12.882 | 12.882 | Pm-3m |
| IRMOF-6 | Zn(NO$_3$)$_2$•4H$_2$O 0.20 mmol [C$_2$H$_4$]-BDC 0.60 mmol | DEF | 90 | 90 | 90 | 25.842 | 25.842 | 25.842 | Fm-3m |
| IRMOF-7 | Zn(NO$_3$)$_2$•4H$_2$O 0.07 mmol 1,4NDC 0.20 mmol | DEF | 90 | 90 | 90 | 12.914 | 12.914 | 12.914 | Pm-3m |
| IRMOF-8 | Zn(NO$_3$)$_2$•4H$_2$O 0.55 mmol 2,6NDC 0.42 mmol | DEF | 90 | 90 | 90 | 30.092 | 30.092 | 30.092 | Fm-3m |
| IRMOF-9 | Zn(NO$_3$)$_2$•4H$_2$O 0.05 mmol BPDC 0.42 mmol | DEF | 90 | 90 | 90 | 17.147 | 23.322 | 25.255 | Pnnm |
| IRMOF-10 | Zn(NO$_3$)$_2$•4H$_2$O 0.02 mmol BPDC 0.012 mmol | DEF | 90 | 90 | 90 | 34.281 | 34.281 | 34.281 | Fm-3m |
| IRMOF-11 | Zn(NO$_3$)$_2$•4H$_2$O 0.05 mmol HPDC 0.20 mmol | DEF | 90 | 90 | 90 | 24.822 | 24.822 | 56.734 | R-3m |
| IRMOF-12 | Zn(NO$_3$)$_2$•4H$_2$O 0.017 mmol | DEF | 90 | 90 | 90 | 34.281 | 34.281 | 34.281 | Fm-3m |

-continued

| MOF-n | Constituents molar ratio M + L | Solvents | α | β | γ | a | b | c | Space group |
|---|---|---|---|---|---|---|---|---|---|
| IRMOF-13 | HPDC 0.12 mmol Zn(NO$_3$)$_2$·4H$_2$O 0.048 mmol | DEF | 90 | 90 | 90 | 24.822 | 24.822 | 56.734 | R-3m |
| IRMOF-14 | PDC 0.31 mmol Zn(NO$_3$)$_2$·4H$_2$O 0.17 mmol | DEF | 90 | 90 | 90 | 34.381 | 34.381 | 34.381 | Fm-3m |
| IRMOF-15 | PDC 0.12 mmol Zn(NO$_3$)$_2$·4H$_2$O 0.063 mmol | DEF | 90 | 90 | 90 | 21.459 | 21.459 | 21.459 | Im-3m |
| IRMOF-16 | TPDC 0.025 mmol Zn(NO$_3$)$_2$·4H$_2$O 0.0126 mmol TPDC 0.05 mmol | DEF NMP | 90 | 90 | 90 | 21.49 | 21.49 | 21.49 | Pm-3m |

ADC Acetylenedicarboxylic acid
NDC Naphthalenedicarboxylic acid
BDC Benzenedicarboxylic acid
ATC Adamantanetetracarboxylic acid
BTC Benzenetricarboxylic acid
BTB Benzenetribenzoic acid
MTB Methanetetrabenzonic acid
ATB Adamantanetetrabenzoic acid
ADB Adamantanedibenzonic acid Further MOFs are MOF-177, MOF-178, MOF-74, MOF-235, MOF-236, MOF-69 to 80, MOF-501, MOF-502, which are described in the literature.

The metalorganic frameworks of the present invention comprise pores, in particular micropores and/or mesopores. Micropores are defined as pores having a diameter of 2 nm or less and mesopores are defined by a diameter in the range from 2 to 50 nm, in each case in accordance with the definition given in Pure & Applied Chem. 57 (1985), 603-619, in particular on page 606. The presence of micropores and/or mesopores can be checked by means of sorption measurements, with these measurements determining the uptake capacity of the MOF for nitrogen at 77 kelvin in accordance with DIN 66131 and/or DIN 66134.

The specific surface area, calculated according to the Langmuir model in accordance with DIN 66135 (DIN 66131, 66134), of a metal organic framework in powder form is preferably more than 5 m$^2$/g, more preferably above 10 m$^2$/g, more preferably more than 50 m$^2$/g, even more preferably more than 500 m$^2$/g, even more preferably more than 1000 m$^2$/g and particularly preferably more than 1250 m$^2$/g.

Shaped MOF bodies can have a lower specific surface area, but preferably more than 10 m$^2$/g, more preferably more than 50 m$^2$/g, even more preferably more than 500 m$^2$/g.

The pore size of the metal organic framework can be controlled by selection of the appropriate ligand and/or the at least bidentate organic compound. It is frequently the case that the larger the organic compound, the larger the pore size. The pore size is preferably from 0.2 nm to 30 nm, particularly preferably in the range from 0.3 nm to 9 nm, based on the crystalline material.

However, larger pores whose size distribution can vary also occur in a shaped MOF body. However, preference is given to more than 50% of the total pore volume, in particular more than 75%, being made up by pores having a pore diameter of up to 1000 nm. However, a large part of the pore volume is preferably made up by pores having two different diameter ranges. It is therefore more preferred for more than 25% of the total pore volume, in particular more than 50% of the total pore volume, to be made up by pores which are in a diameter range from 100 nm to 800 nm and for more than 15% of the total pore volume, in particular more than 25% of the total pore volume, to be made up by pores which are in a diameter range up to 10 nm. The pore distribution can be determined by means of mercury porosimetry.

The metal organic framework can be present in powder form or as agglomerates. The framework can be used as such or is converted into a shaped body. Preferred processes here are extrusion or tableting. In the production of shaped bodies, the framework can be mixed with further materials such as binders, lubricants or other additives which are added during production. It is likewise conceivable for the framework to be mixed with further constituents, for example adsorbents such as activated carbon or the like.

The possible geometries of the shaped body are in principle not subject to any restrictions. For example, possible shapes are, inter alia, pellets such as disk-shaped pellets, pills, spheres, granules, extrudates such as rods, honeycombs, grids or hollow bodies.

To produce the shaped bodies, it is in principle possible to employ all suitable methods. In particular, the following processes are preferred:

Kneading/pan milling of the framework either alone or together with at least one binder and/or at least one pasting agent and/or at least one template compound to give a mixture; shaping of the resulting mixture by means of at least one suitable method such as extrusion; optionally washing and/or drying and/or calcination of the extrudate; optionally finishing treatment.

Application of the framework to at least one optionally porous support material. The material obtained can then be processed further by the above-described method to give a shaped body.

Application of the framework to at least one optionally porous substrate.

Kneading/pan milling and shaping can be carried out by any suitable method, for example as described in Ullmanns Enzyklopädie der Technischen Chemie, 4th edition, volume 2, p. 313 ff. (1972).

For example, the kneading/pan milling and/or shaping can be carried out by means of a piston press, roller press in the presence or absence of at least one binder, compounding, pelletization, tableting, extrusion, coextrusion, foaming, spinning, coating, granulation, preferably spray granulation, spraying, spray drying or a combination of two or more of these methods.

Very particular preference is given to producing pellets and/or tablets.

The kneading and/or shaping can be carried out at elevated temperatures, for example in the range from room temperature to 300° C., and/or under superatmospheric pressure, for example in the range from atmospheric pressure to a few hundred bar, and/or in a protective gas atmosphere, for example in the presence of at least one noble gas, nitrogen or a mixture of two or more thereof.

The kneading and/or shaping is, in a further embodiment, carried out with addition of at least one binder, with the binder used basically being able to be any chemical compound which ensures the desired viscosity for the kneading and/or shaping of the composition to be kneaded and/or shaped. Accordingly, binders can, for the purposes of the present invention, be either viscosity-increasing or viscosity-reducing compounds.

Preferred binders are, for example, inter alia aluminum oxide or binders comprising aluminum oxide, as are described, for example, in WO 94/29408, silicon dioxide as described, for example, in EP 0 592 050 A1, mixtures of silicon dioxide and aluminum oxide, as are described, for example, in WO 94/13584, clay minerals as described, for example, in JP 03-037156 A, for example montmorillonite, kaolin, bentonite, hallosite, dickite, nacrite and anauxite, alkoxysilanes as described, for example, in EP 0 102 544 B1, for example tetraalkoxysilanes such as tetramethoxysilane, tetraethoxysilane, tetrapropoxysilane, tetrabutoxysilane, or, for example, trialkoxysilanes such as trimethoxysilane, triethoxysilane, tripropoxysilane, tributoxysilane, alkoxytitanates, for example tetraalkoxytitanates such as tetramethoxytitanate, tetraethoxytitanate, tetrapropoxytitanate, tetrabutoxytitanate, or, for example, trialkoxytitanates such as trimethoxytitanate, triethoxytitanate, tripropoxytitanate, tributoxytitanate, alkoxyzirconates, for example tetraalkoxyzirconates such as tetramethoxyzirconate, tetraethoxyzirconate, tetrapropoxyzirconate, tetrabutoxyzirconate, or, for example, trialkoxyzirconates such as trimethoxyzirconate, triethoxyzirconate, tripropoxyzirconate, tributoxyzirconate, silica sols and/or amphiphilic substances.

As viscosity-increasing compound, it is, for example, also possible to use, if appropriate in addition to the abovementioned compounds, an organic compound and/or a hydrophilic polymer such as cellulose or a cellulose derivative such as methylcellulose and/or a polyacrylate and/or a polymethacrylate and/or a polyvinyl alcohol and/or a polyvinylpyrrolidone and/or a polyisobutene and/or a polytetrahydrofuran and/or a polyethylene oxide.

As pasting agent, it is possible to use, inter alia, preferably water or at least one alcohol such as a monoalcohol having from 1 to 4 carbon atoms, for example methanol, ethanol, n-propanol, isopropanol, 1-butanol, 2-butanol, 2-methyl-1-propanol or 2-methyl-2-propanol or a mixture of water and at least one of the alcohols mentioned or a polyhydric alcohol such as a glycol, preferably a water-miscible polyhydric alcohol, either alone or as a mixture with water and/or at least one of the monohydric alcohols mentioned.

Further additives which can be used for kneading and/or shaping are, inter alia, lubricants such as graphites, amines or amine derivatives such as tetraalkylammonium compounds or amino alcohols and carbonate-comprising compounds such as calcium carbonate. Such further additives are described, for instance, in EP 0 389 041 A1, EP 0 200 260 A1 or WO 95/19222.

The order of the additives such as template compound, binder, pasting agent, viscosity-increasing substance during shaping and kneading is in principle not critical.

In a further, preferred embodiment, the shaped body obtained by kneading and/or shaping is subjected to at least one drying step which is generally carried out at a temperature in the range from 25 to 300° C., preferably in the range from 50 to 300° C. and particularly preferably in the range from 100 to 300° C. It is likewise possible to carry out drying under reduced pressure or under a protective gas atmosphere or by spray drying.

In a particularly preferred embodiment, at least one of the compounds added as additives is at least partly removed from the shaped body during this drying process.

The present invention further provides for the use of a porous metal organic framework according to the invention as ion exchanger, Brönsted acid or support material. The porous frameworks can be used, for example, in chemical reactions such as esterifications, etherifications, transesterifications, transetherifications, alkylations, acylations, isomerizations, dehydrations and hydrations, alkoxylations, dimerizations, oligomerizations and polymerizations and also aminations.

EXAMPLES

Example 1

Preparation of an Aluminum Metal Organic Framework ("Al-MOF")

250.1 g of terephthalic acid (BDC) and 292.9 g of $Al_2(SO_4)_3 \cdot 18H_2O$ are suspended in 1.257 g of N,N-dimethylformamide (DMF) and heated at 130° C. for 24 hours while stirring. The suspension is subsequently filtered and the filtrate is washed with DMF. The filter cake is dried at 120° C. in a drying oven for 2 hours. It is subsequently calcined at 320° C. in a muffle furnace for 2 hours.

Example 2

Preparation of a Sulfonated Al-MOF According to the Invention 3.0 g of the Al-MOF powder from example 1 are introduced into an exchange tube made of glass and provided with a P3 glass frit and heated to 80° C. under nitrogen (16 standard l/h). The powder is then reacted at 80° C. with 1.2 g of gaseous sulfur trioxide over a period of 5 minutes. After the reaction, the powder is dried at 50° C. and 100 mbar for 16 hours.

The surface area (BET) is found to be 494 $m^2/g$. The XRD is shown in FIG. 1, wherein I (Lin (counts)) is shown as function of 2Θ (2-Theta Scale).

Elemental analysis indicates an S:C ratio of 1:31. The Al:S ratio is about 7:1. From this it is possible to calculate an acid density of about 1.0 mmol/g for the sulfonated Al-MOF powder.

Example 3

Acid-Catalyzed Esterification of Butanol with Acetic Acid Using a Metal Organic Framework According to the Invention In a 100 ml three-necked flask provided with a reflux condenser, 50 g of a butanol:acetic acid (67:33% by weight) mixture are admixed with 1.0 g of sulfonated Al-MOF from example 2 and stirred. The mixture is then heated to 75° C. and a sample is taken after a reaction time of 6 hours. The sample is subsequently analyzed by gas chromatography to determine its composition. It comprises 7% by area of acetic acid, 58% by area of butanol and 35% by area of butyl acetate.

Comparative Example 4

Esterification of Butanol with Acetic Acid Over a Nonsulfonated MOF

The experiment is carried out in a manner analogous to example 3, but 1.0 g of Al-MOF powder from example 1 is used here. The sample after a reaction time of 5.5 hours comprises 11% by area of acetic acid, 73% by area of butanol and 16% by area of butyl acetate.

The invention claimed is:

1. A porous metal organic framework comprising at least one at least bidentate organic compound L coordinated to at least one metal ion M, wherein L has at least one functional group G which bonds noncoordinatively to M and is selected from the group consisting of —$SO_3H$ and their deprotonated analogue.

2. The framework according to claim 1, wherein the molar ratio of G:M is at least 1:75.

3. The framework according to claim 1, which has an acid density of at least 0.1 mmol/g of framework.

4. The framework according to claim 1, wherein M is selected from the group consisting of Mg, Ca, Al, Ga, In, Zn, Cu, Fe and Mn.

5. The framework according to claim 1, wherein L is derived from a dicarboxylic, tricarboxylic, tetracarboxylic acid or a sulfur analogue or a diamine.

6. A process for preparing a framework according to claim 1, which comprises the step contacting of a metal ion M with an optionally deprotonated at least bidentate organic compound L which has at least one functional group G which bonds noncoordinatively to M and is selected from the group consisting of —SO3H and their deprotonated analogue to form the framework.

7. A process for preparing a framework according to claim 1, which comprises the steps contacting of a metal ion M with an optionally deprotonated at least bidentate organic compound L' which has at least one S-comprising group G' which preferably bonds noncoordinatively to M and conversion of the group G' into a group G on L.

8. The process according to claim 7, wherein G' is a sulfonate, sulfite, disulfite, sulfinate group or a corresponding acid, ester or halide, mercapto or phosphine group.

9. A process for preparing a framework according to claim 1, which comprises the steps reaction of a porous metal organic framework comprising at least one at least bidentate organic compound L' coordinated to at least one metal ion M containing an aromatic or a vinylic double bond with an S-comprising compound to form a group G on L or a group G' on L and if G' is present, conversion of G' into G.

* * * * *